United States Patent [19]

Gilbaugh

[11] Patent Number: 4,892,520
[45] Date of Patent: Jan. 9, 1990

[54] FINGER MOUNTED SURGICAL NEEDLE GUIDE/NEEDLE PROTECTOR

[76] Inventor: James H. Gilbaugh, 2902 SW. Canterbury La., Portland, Oreg. 97201

[21] Appl. No.: 226,796

[22] Filed: Aug. 1, 1988

Related U.S. Application Data

[63] Continuation-in-part of Ser. No. 218,229, Jul. 13, 1988.

[51] Int. Cl.⁴ .............................................. A61M 5/00
[52] U.S. Cl. .................................. 604/117; 604/164; 604/272
[58] Field of Search ............... 604/263, 164, 117, 116, 604/180, 308, 272

[56] References Cited

U.S. PATENT DOCUMENTS 2,880,724 4/1959 Velarde .
3,595,217 7/1971 Rheinfrank .
3,741,211 6/1973 Vreeland, Jr. .
4,555,243 11/1985 Markham .

Primary Examiner—Stephen C. Pellegrino
Attorney, Agent, or Firm—Kolisch, Hartwell & Dickinson

[57] ABSTRACT

A finger mountable surgical needle guide/needle protector. The guide includes an elongate body divided by a flangible web into two segments. A needle-receiving lumen extends through the body for holding a needle protectively sheathed prior to a surgical procedure, and for guiding the needle slidably during such a procedure. A needle is guided under a circumstance with the two body segments separated, and with only one of these segments then employed. An end of this employed segment acts to assist a surgeon in controlling the depth of needle penetration. Extending from the distal end of the procedure-employed body segment is an elongate, touch-sensitive paper ribbon which extends over the finger tip and allows a surgeon easily to feed for an anomaly which is to be investigated.

8 Claims, 2 Drawing Sheets

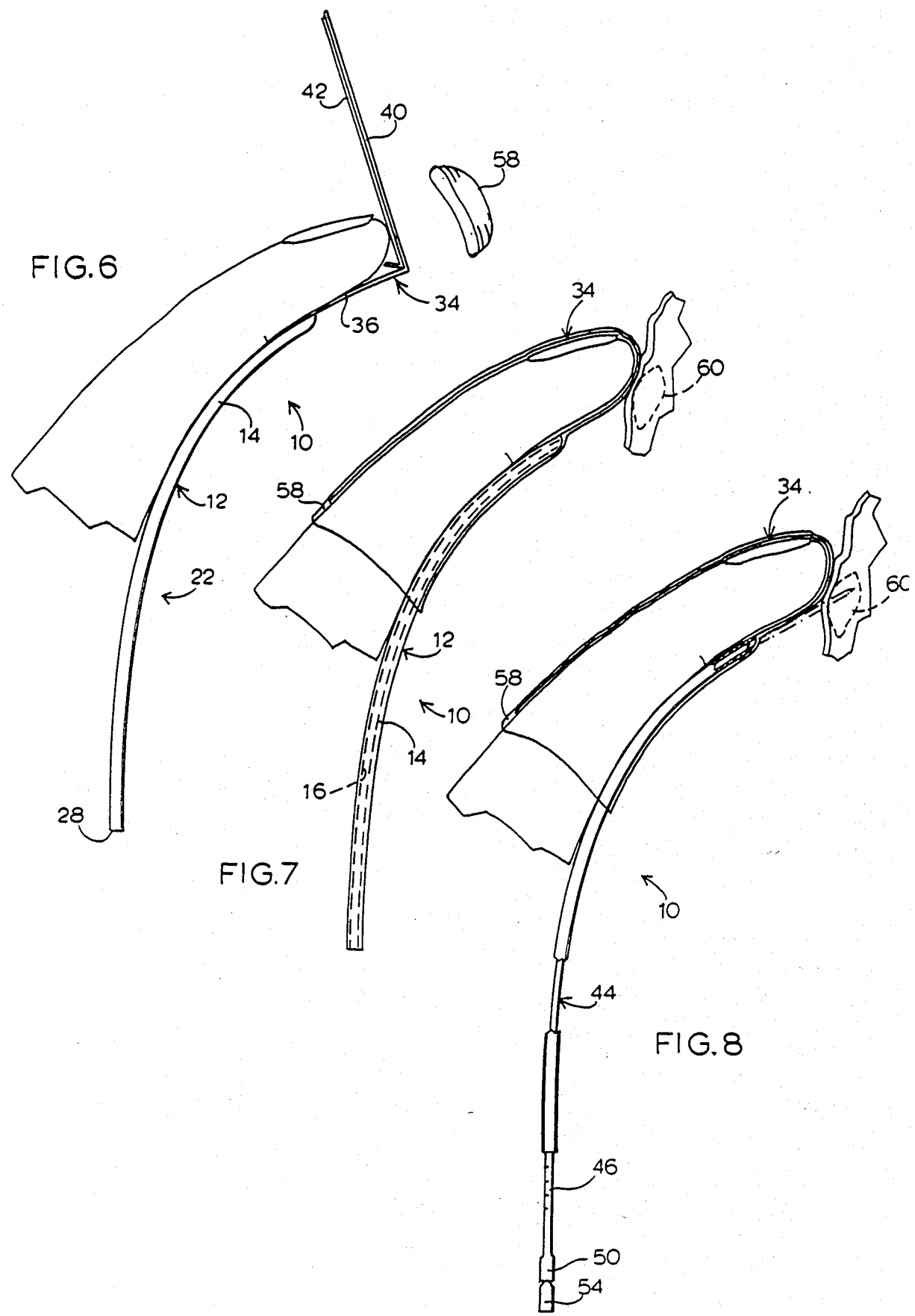

FINGER MOUNTED SURGICAL NEEDLE GUIDE/NEEDLE PROTECTOR

This is a continuation-in-part of application Ser. No. 218,229, filed July 13, 1988.

BACKGROUND AND SUMMARY OF THE INVENTION

This invention relates to a surgical needle guide, and specifically to a needle guide which may be secured to a physician/surgeon's gloved finger to guide a needle in the course of a surgical procedure, such as in the examination of the prostate gland.

Some surgical procedures require that a surgeon manually direct an aspiration or biopsy surgical needle to adjacent tissue which is to be sampled during a surgical procedure. A variety of devices which assist in guiding such a needle have been disclosed. However, known devices do not provide readily for temporary precise attachment of a device on a surgeon's finger, nor do they allow a surgeon to palpate, with virtually no obstruction, and with a high degree of tactility, the patient's tissue while positioning the device and an associated needle A key object of the present invention is to provide a finger-mount surgical needle guide which significantly advances the state of the art in such devices More particularly, an object of the invention is to provide such a guide which is readily placed, in a precise predetermined position, on a surgeon's finger Another object is to provide, in such a guide, a pliable, touch-sensitive ribbon/attaching web which allows a surgeon, with the guide in place, and using the entirety of his or her finger tip, to palpate a patient's body tissue to assure proper relative positioning of the needle guide, and hence of a needle guided by the guide A further object of the invention is to provide a guide of the type outlined which is effective to help indicate the depth of needle insertion in the patient's tissue.

A related object is to provide such a guide which includes two separable segments, joined by a frangible web which allows for easy separation. Unseparated, the overall guide can house a fully sheathed, fully protected needle in a preassembled, sterile, pre-use package. Separated, one of the segments acts as the final procedure guide, with an end functioning to alert the surgeon about, and to control, the depth of needle penetration.

The proposed guide includes an elongate body, with a flexible central needle support having a lumen which receives and guides a surgical needle Forming part of the body is an integral wing-like structure which extends laterally from opposite sides of the support along its length. An elongate guide attaching ribbon extends from the distal end of the body. This ribbon includes a first portion which has a predetermined length extending immediately beyond the distal end of the guide body. This first portion acts, in part, as a measure for aligning the distal end of the body properly relative to the tip of a surgeon's finger A second portion in the ribbon extends initially at an angle from the first portion, assists in the aligning process, and functions for training, or folding, smoothly over and around the top of a surgeon's finger tip. The first and second ribbon portions bear an adhesive which is usable to secure the guide in place These ribbon portions take the form of a flexible, thin web which promotes finger touch-sensitivity to allow ready, informative palpating of the patient's body tissue properly to position a needle for a surgical procedure The ribbon portions also act as what might be thought of as a glance protector over the end of the finger to protect against injury during surgery.

According to a modified form of the invention, instead of there being, as viewed in cross-section, a distinct lumen structure with wing-like lateral extensions, the cross-sectional configuration of the modified device, along substantially all of its length, takes the form, generally, of a segment of a circle. A bore extends generally centrally through this cross section to define a needle-receiving passage.

These and other objects and advantages offered by the invention will become more fully apparent as the description which now follows is read in conjunction with the accompanying drawings.

DESCRIPTION OF THE DRAWINGS

FIG. 6 depicts preliminary positioning and securing of the guide of the invention on a surgeon's gloved finger FIGS. 7 and 8 relate to FIG. 6, and depict successive steps in a surgical procedure.

FIG. 9 is a transverse cross-sectional view of a modified form of the needle guide of the invention.

DETAILED DESCRIPTION OF THE PREFERRED EMBODIMENT

Figure 1:
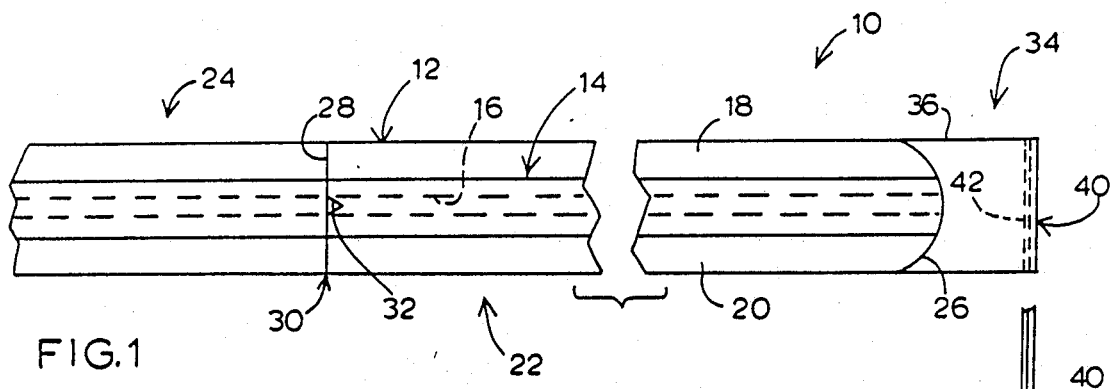
FIG. 1 is a fragmentary top plan view of the needle guide of the invention.
Figure 2:
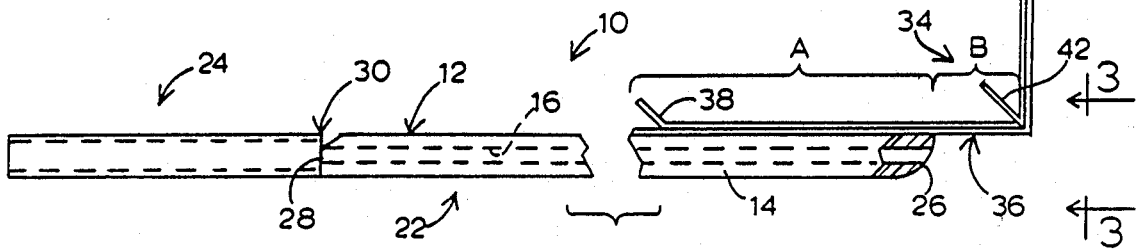
FIG. 2 is a fragmentary side view of the guide in FIG. 1, taken from the top side of the latter.
Figure 3:
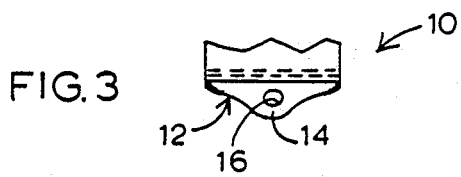
FIG. 3 is fragmentary end view of the distal end of the guide, taken generally along the line 3—3 in FIG. 2.

Referring now to the drawings, and initially to FIGS. 1-3, inclusive, a finger-mounted (or finger-mount) surgical needle guide is shown generally at 10. Guide 10 includes an elongate body 12 having a central needle support 14, with a lumen 16 extending therethrough. Lumen 16 is sized appropriately to receive a selected type of surgical needle having a predetermined (known) diameter.

Body 12 further includes wings 18, 20 which extend laterally on opposite sides of support 14. These are integral with the support 14. Wings 18, 20 define a generally flat mounting/stabilizing surface for placement of the guide against the underside of a surgeon's finger.

Body 12 also includes first and second segments 22, 24. First segment 22 is of a predetermined length, which is less than that of the selected surgical needle which will be used in a procedure. The distal 26 of segment 22 is formed with curvature to eliminate sharp corners. The other (proximal) end 28 of segment 22 is severably joined to segment 24 through a frangible web 30. As will be explained, end 28 serves as a reference point, or register, to help establish and control needle penetration depth during a procedure. A tapered needle insertion mouth 32 is formed as a lateral opening in the wall of support 14. This serves to gather, capture and direct the sharp tip of a surgical needle into lumen 16 during a procedure.

Second segment 24 has a length which, with the first and second segments joined, establishes an overall length sufficient fully to sheath a needle in a pre-procedure stored and protected condition.

A thin, touch-sensitive, attaching ribbon 34 extends from the distal end of body 12. Ribbon 34 includes a first portion 36 which is secured to the back side of body 12 along a length A, as by an adhesive A second, predetermined length B extends beyond the distal end of body 12. This, as will be explained, accommodates accurate positioning of body 12 on the palmar of a surgeon's finger A first tab adhesive-covering 38 is secured to the back side of portion 36.

Ribbon 34 includes a second portion 40 which extends (initially at an angle) beyond first portion 36. This cooperates with length B in portion 36 for aligning the guide longitudinally relative to a surgeon's finger tip The aligning process will be described shortly Second portion 40 also has an adhesive coating on the rear side thereof which is protected by a second tab 42. Both ribbon portions 36 are formed of a pliable, thin slick-surface-treated paper material. They are shown with their thicknesses greatly exaggerated in the drawings. Ribbon 34 is constructed preferably of such a material which promotes, completely around a surgeon's finger tip, touch-sensitivity to allow for highly informative palpating of the selected surgical area in a patient's body to be considered for aspiration or biopsy. This is an extremely important feature of the invention. It offers the entire finger tip (tip and base) the opportunity to feel for the telltale sign of an anomaly to be probed during a procedure. This same structure, significantly, also acts as a glance-protective barrier over a surgeon's finger tip to prevent finger injury.

While length A in ribbon portion 36 is shown herein to be relatively long, it could, of course, be shortened, with adhesive then made available along the length of body 12 no longer covered by the revised-length ribbon.

Let us consider now FIGS. 4 and 6-8, inclusive. Reference will be made to these four figures in connection with preparing for and performing a surgical aspiration procedure of the prostate gland.

Figure 4:
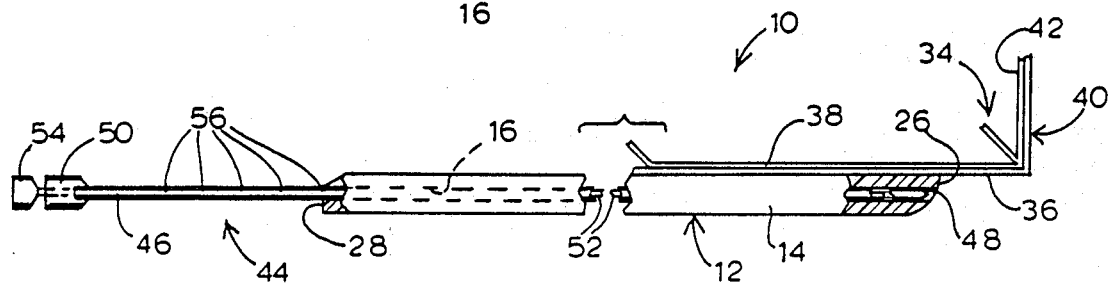
FIG. 4 is a fragmentary side view of the guide, with the same shown holding a surgical aspiration needle during one stage in the preparation for a surgical procedure.

The guide of the present invention, in this instance, is constructed in such a fashion that lumen 16 is sized to receive an aspiration needle, such as needle 44 in FIG. 4. This aspiration needle, which is entirely conventional in construction, includes the usual hollow needle body 46, having a sharpened end 48, and a proximal fluid end connector 50 The needle also includes the usual central stylet 52 which fits freely and slidably within the hollow interior of body 46. The overall length of stylet 52 is just slightly less than that of body 46. The proximal end of the stylet carries a manipulation knob 54.

Marked along the outside of body 46, adjacent connector 50, are plural indicia marks, such as those shown at 56, which will be employed, as will be explained, to aid a surgeon in determining the depth of penetration of end 48 during a surgical procedure. While other specific indicia patterns may be used, each indicia mark 56 herein is spaced from the next adjacent one by about 1 cm. The right-most mark 56 in FIG. 4 is positioned along the body in such a fashion that, when this mark is located at the position of end 28 (the region of joinder with segment 24), sharp end 48 in the needle is just short of emerging from the distal end of lumen 16. This condition is illustrated in FIG. 4.

The present invention contemplates that the needle guide will be presented in a sterile package, along with the appropriate surgical needle, such as needle 44, fully sheathed To begin a procedure, the surgeon gloves his or her hand, opens the sterile package, removes the needle from guide 10, and breaks away guide segment 24.

Thereafter, the surgeon peels away tab 38, and places the guide on the palmar side of the forefinger in a position where the finger tip just touches the tab-protected part of ribbon portion 40. This condition is illustrated in FIG. 6. The just-exposed adhesive surface, exposed by removal of tab 38, is pressed against the palmar side of the finger, and tab 42 is then removed to expose the adhesive surface on ribbon portion 40. This portion is then pulled and folded smoothly around the finger tip, and adhered to the outer, upper side of the gloved finger. A thin, rubber, condom-like cot 58 is then pulled down over this entire structure to stabilize it on the end of the finger. The surgeon then feels for the suspicious area digitally.

Next, typically, the surgeon inserts needle 44 to a position where the sharpened end 48 is just short of the distal end of lumen 16 This is the condition illustrated in FIG. 4, which condition is facilitated by placing the distal-most indicia mark 56 relative to the former position of frangible web 30—namely, the "now" proximal end 28 of guide 10.

The surgeon's finger is manipulated to place it adjacent the prostate gland (see FIG. 7 wherein the needle is not shown), and the surgeon palpates that body area to feel for the presence of, for example, a suspect nodule such as that shown at 60. This tactile procedure is greatly facilitated by the fact that ribbon 34, extending as it does over the entirety of the tip of the surgeon's finger, readily promotes feeling for an anomaly such as this nodule. The entire finger tip is made capable of necessary tactile sensation.

With this part of the procedure completed, the surgeon extends the needle from the guide by advancing it in the guide (see FIG. 8), monitoring its depth penetration by observing the positions of the indicia marks relative to the proximal end (28) of the guide With proper depth penetration achieved, the stylet is removed, and coupling 50 is connected to the usual fluid aspirator, whereafter, following aspiration, the needle is withdrawn, and the finger (with guide) removed. As a safety measure against the possible transfer of disease, the guide is then discarded.

Figure 5:
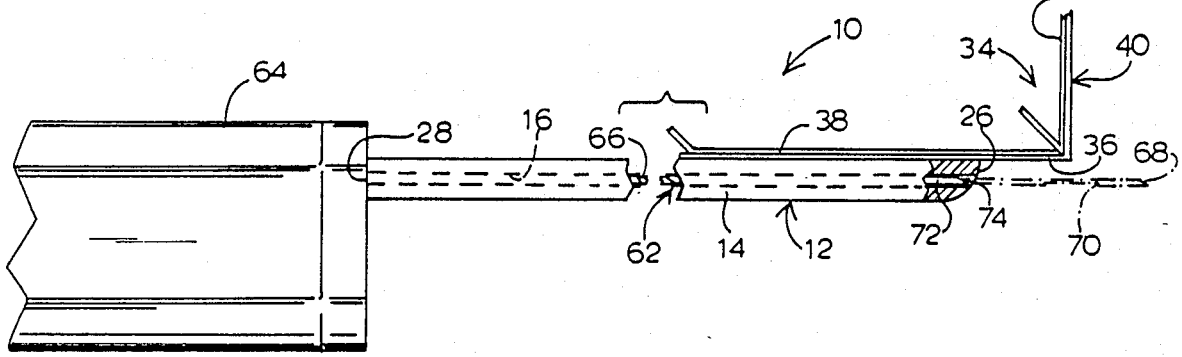
FIG. 5 is a fragmentary side view of the guide, with the same shown holding a biopsy surgical needle in a preparation stage like that depicted in FIG. 4.

Considering now a biopsy procedure, and referring to FIG. 5, here, guide 10 is shown with a conventional surgical biopsy needle 62. Needle 62 is illustrated mounted in a conventional spring-powered driver 64. Needle 62 includes an inner needle 66, which has, as can be seen in a dashed-line, extended condition, a pointed end 68, and a cut-away notch 70 formed adjacent end 68. A hollow sleeve 72 encases inner needle 66, and includes a forward, cutting edge 74. Guide 10 and needle 62 are constructed and arranged such that, with guide segments 22, 24 separated, when needle 62 is retained by driver 64, and, when the right end of the driver (in FIG. 5) butts against guide segment end 28, cutting edge 74 of the outer needle is held just within the confines of the distal end of lumen 16. Inner needle 66 resides, under these circumstances, within the confines of outer needle 72.

Employing needle 62, the same kinds of preliminary steps described earlier in conjunction with needle 44 are employed, vis-a-vis mounting of the guide on a surgeon's finger, and palpating of the surgical area to determine precisely where a biopsy is to take place.

With this done, needle 62, carried by driver 64, is inserted in lumen 16 to a point where the right end (again see FIG. 5) of the driver butts against guide segment end 28. The firing mechanism in the driver is then triggered, whereupon the inner and outer needle portions of needle 62 function in the usual manner to capture a biopsy sample.

As was mentioned earlier, driver 64 is conventional in construction, and is designed to operate the components of needle 64 in such a fashion that, with the distal end of this driver butting against end 28, the depth of needle penetration is precisely controlled. Thus, here also, the break-away exposed end 28 in guide segment 22 acts to assist a surgeon in precise depth positioning during a surgical procedure.

Thus, a preferred embodiment of the proposed surgical needle guide has been described. In its initial, unaltered state, the guide acts an as initial receptacle for a selected surgical needle, receiving the same in a protected and fully sheathed condition within lumen 16. During a procedure, separable segments in the guide body are broken away from one another, with the distal segment 22 thereafter acting as the finally useable depth-control/guide portion during a procedure The initially angulated, thin, flexible ribbon 34 which extends from the distal end of the guide body, adjacent one side of lumen 16, acts conveniently to assist a surgeon in positioning the guide properly longitudinally relative to his or her forefinger tip. This ribbon, with positioning accomplished, then pulled smoothly and folded around a surgeon's gloved finger tip, functions both to promote a high degree of informative tactile palpation capability during a procedure, and at the same time to provide glance protection against injury to the surgeon's finger.

Focusing attention now briefly on FIG. 9, here there is shown a transverse cross-sectional view of a modified form (second embodiment) of a needle guide, designated 60. Guide 60 is, in all respects other than those which will now be described specifically, identical in construction to guide 10. Because of this, views of the modified guide, other than that appearing in FIG. 9, are not presented.

The key distinction between guide 60 and guide 10 is that the former does not include a distinct central lumen structure with lateral wings, like wings 18, 20. Rather, guide 60 has a cross sectional which is generally like that of a segment of a circle. Thus, this cross section includes a curvilinear (preferably, but not necessarily, circular) boundary 60a, and a linear boundary 60b. A lumen 62 (which is like previously described lumen 16) extends generally centrally through this segment-like cross section.

During use, it is the flat side, the side defined by boundary 60b of the profile, which lies adjacent a surgeon's finger.

An important advantage offered by guide 60, in procedures with patients who may be contact-agitated by the more irregular cross-sectional contour of a guide like guide 10, is that the smoothly curved surface defined by boundary 60a tends to minimize any likelihood of such agitation.

Obviously, the guide proposed by this invention (both embodiments) is extremely simple in construction, low in cost, and convenient, accurate and easy to use.

Preferably, the guide is made to be disposable for obvious reasons.

Accordingly, while a preferred embodiment of the invention, and a modification thereof, have been described, other variations and modifications are of course possible without departing from the spirit of the invention.

It is claimed and desired to be secured by Letters Patent:

1. A finger-mount guide for a surgical needle comprising
   an elongate, finger-mountable, body having proximal and distal ends with an open lumen extending between said ends for receiving, freely and slidably, such a needle, and
   an elongate, flexible, touch-sensitive, glance-protective attaching ribbon joined to said body adjacent, and extendible from, the latter's said distal end adjacent one side of the distal end of said lumen, adapted for folding longitudinally smoothly around the end of the user's finger with the guide in place on the finger, thus to promote, for the user, touch sensitivity, and finger/needle protectivity, during a guided surgical procedure.

2. The guide of claim 1, wherein said body includes a pair of elongate body segments joined through a frangible web.

3. The guide of claim 2 which further includes a lateral entry mouth open to a side of said lumen within the body adjacent one side of said frangible web.

4. The guide of claim 2, wherein the end of one of said body segments adjacent said frangible web is structured to act as a depth penetration control.

5. The guide of claim 1, wherein said body is characterized by a transverse cross section that has a segment-like configuration including a curvilinear portion.

6. The guide of claim 5, wherein said body includes a pair of elongate body segments joined through a frangible web.

7. The guide of claim 6 which further includes a lateral entry mouth open to a side of said lumen within the body adjacent one side of said frangible web.

8. The guide of claim 6, wherein the end of one of said body segments adjacent said frangible web is structured to act as a depth penetration control.

* * * * *